(12) United States Patent
Campbell et al.

(10) Patent No.: US 6,348,068 B1
(45) Date of Patent: Feb. 19, 2002

(54) MULTI-FILAMENT VALVE STENT FOR A CARDISC VALVULAR PROSTHESIS

(75) Inventors: Louis A. Campbell, Austin; James Henry Hamblin, Jr., Lockhart, both of TX (US)

(73) Assignee: Sulzer Carbomedics Inc., Austin, TX (US)

( * ) Notice: Subject to any disclaimer, the term of this patent is extended or adjusted under 35 U.S.C. 154(b) by 0 days.

(21) Appl. No.: 09/360,127

(22) Filed: Jul. 23, 1999

(51) Int. Cl.[7] ................................................. A61F 2/24
(52) U.S. Cl. ...................... 623/2.36; 623/1.15; 623/2.14
(58) Field of Search ............................ 623/1.15, 1.33, 623/1.49, 1.53, 1.54, 2.14, 2.17, 2.18, 2.36, 2.37, 2.38, 900

(56) References Cited

U.S. PATENT DOCUMENTS

| | | | |
|---|---|---|---|
| 3,463,158 A | * 8/1969 | Schmitt et al. | 623/1.53 |
| 3,656,185 A | 4/1972 | Carpentier | 3/1 |
| 4,042,979 A | 8/1977 | Angell | 3/1.5 |
| 4,055,861 A | 11/1977 | Carpentier et al. | 3/1.5 |
| 4,106,129 A | 8/1978 | Carpentier et al. | 3/1.5 |
| 4,144,046 A | 3/1979 | Esposito | 71/86 |
| 4,164,046 A | 8/1979 | Cooley | 3/1.5 |
| 4,290,151 A | 9/1981 | Massana | 3/1.5 |
| 4,343,048 A | 8/1982 | Ross et al. | 3/1.5 |
| 4,489,446 A | 12/1984 | Reed | 3/1.5 |
| 4,501,030 A | 2/1985 | Lane | 3/1.5 |
| 5,037,434 A | 8/1991 | Lane | 623/2 |
| 5,061,277 A | 10/1991 | Carpentier et al. | 623/2 |
| 5,104,407 A | 4/1992 | Lam et al. | 623/2 |
| 5,147,400 A | * 9/1992 | Kaplan et al. | 623/13 |
| 5,306,296 A | 4/1994 | Wright et al. | 623/2 |
| 5,489,297 A | * 2/1996 | Duran | 623/2.17 |
| 5,545,215 A | 8/1996 | Duran | 623/2 |
| 5,562,729 A | 10/1996 | Purdy et al. | 623/2 |
| 5,593,424 A | 1/1997 | Northrup, III | 606/232 |
| 5,612,885 A | * 3/1997 | Love | 623/900 |
| 5,716,397 A | 2/1998 | Myers | 623/2 |
| 5,855,598 A | 1/1999 | Pinchuk | 623/1 |
| 5,871,535 A | * 2/1999 | Wolff et al. | 623/1.42 |
| 5,919,225 A | * 7/1999 | Lau et al. | 623/1.13 |
| 5,957,974 A | * 9/1999 | Thompson et al. | 623/1.13 |
| 6,083,257 A | * 7/2000 | Tayor et al. | 623/1.53 |
| 6,156,064 A | * 12/2000 | Chouinard | 623/1.44 |

FOREIGN PATENT DOCUMENTS

| | | |
|---|---|---|
| EP | 0 615 769 A1 | 9/1994 |
| EP | 923912 A2 | 6/1999 |

* cited by examiner

Primary Examiner—David H. Willse
Assistant Examiner—Suzette J. Jackson
(74) Attorney, Agent, or Firm—Timothy L. Scott

(57) ABSTRACT

A prosthetic cardiac valvular member of flexible material includes a flexible stent member which may be either attached to the cardiac valvular member or molded therein. The stent member is formed by a plurality of adjacent filaments which are bound together by suturing, braiding, jacketing or encapsulating. The prosthetic cardiac valvular member may be either a flexible heart valve or an annuloplasty ring. Post members are formed into the stent member when the stent member is used in the flexible heart valve.

13 Claims, 4 Drawing Sheets

MULTI-FILAMENT VALVE STENT FOR A CARDISC VALVULAR PROSTHESIS

BACKGROUND

The disclosures herein relate generally to a cardiac valvular prosthesis and more particularly to stents used to reinforce such prostheses.

Heart valves constructed on stents are much easier to implant than stentless valves. Valves with stents often have inferior performance and durability that has been partially attributed to the loss of flexibility with a tissue or polymer valve that occurs when the valve is attached to a rigid stent. A small diameter wire or polymer material has been used to maintain some flexibility in a stent. Polymer stents can loose their shape from repeated loading at body temperature as a result of a process called stent creep. Under extreme loads, polymers can also plastically yield into an undesirable shape. Finally, plastic materials for permanent implants are difficult to obtain. Using a small diameter wire can provide flexibility, but small diameter wires can be easily deformed past their yield point causing permanent deformation of the valve. As the wire diameter gets smaller, the strain on the wire goes up for any given loading situation, therefore, smaller diameter wires are more likely to fail from fatigue.

Various stented valve devices have been proposed. U.S. Pat. No. 4,106,129 discloses a supported bioprosthetic heart valve in which the supporting stent is capable of annular deformation and also of limited perimetric expansion and contraction during heart operation. The stent includes a wire frame composed of a single flexible wire preformed to define inverted U-shaped commissure supports merging smoothly with arcuate portions connecting such supports.

In U.S. Pat. No. 4,343,048, a stent for a cardiac valve comprises a method base ring having metal legs projecting therefrom in a generally axial direction, each leg being flexible in such a manner that, when the stent has a valve installed therein and the valve is under pressure such as when operating in the heart, each respective leg can resiliently deform over substantially its whole axial length to take up strain in the valve without impairing its performance.

U.S. Pat. No. 4,501,030 discloses a prosthetic heart valve including a frame having a plurality of commissure supports, a plurality of resilient supports, and a plurality of valve leaflets. The valve leaflets are attached to the resilient supports, and the resilient supports lie radially outwardly of the commissure supports, respectively. When in use, the valve is subjected to forces which are used to clamp the valve leaflets between the resilient supports and the commissure supports to augment whatever other leaflet attachment techniques may be used.

U.S. Pat. No. 5,037,434 discloses a bioprosthetic heart valve comprising first and second mechanisms for supporting leaflets to provide multiple effective spring constants. An inner frame supporting commissures of the valve is elastic, permitting the commissures to bend in toward the center of the prosthetic heart valve at very low loads. A relatively rigid annular support ring supports the elastic frame and provides the second spring constant mechanism. An attachment system for sewing bioprosthetic leaflets to the frame and clamping the leaflets between the frame and the annular ring minimizes stress risers in the leaflets. The leaflets have an uncoupled mating edge where the leaflets meet in the center of the valve. The uncoupled portions of the leaflets permit the leaflets to roll by each other.

U.S. Pat. No. 5,545,215 discloses a frame to be placed as an external support of a biological valved conduit containing three leaflets. This external frame, made of biocompatible metal or plastic is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle shaped paraboloid gaps result. The frame is a wire-like structure.

U.S. Pat. No. 5,562,729 discloses a multi-leaflet heart valve composed of biocompatible polymer which simultaneously imitates the structure and dynamics of biological heart valves. The valve includes a plurality of flexible leaflets dip cast on a mandrel. The leaflets are then bonded with a bonding agent to the interior surfaces of a plurality of struts on a metal-reinforced prosthetic stent. The leaflets open and close in response to the pumping action of the heart.

There are several commonly known forms of annuloplasty rings. As a result there are three general divisions within the technology for annuloplasty rings. These divisions are stiff vs. flexible rings, partial vs. complete rings and adjustable vs. non-adjustable rings.

A conventional ring, disclosed in U.S. Pat. No. 4,055,861, completely surround the mitral or tricuspid valve annulus with the intent of supporting the entire annulus to prevent dilatation of the natural tissue. U.S. Pat. No. 4,144,046 discloses an early use of a flexible, partial ring. Subsequently, U.S. Pat. No. 4,164,046 disclosed an incomplete or partial ring that reinforces the posterior portion of the mitral valve annulus but does not extend across the anterior portion of the annulus. It was believed by many that the fibrous anterior portion of the annulus is not subject to dilatation, in contrast to the muscular posterior portion of the annulus. Operative time can be reduced with the implantation of a partial ring because fewer sutures are required to secure the ring to the native valve annular tissue. Further, there is some risk of damaging the aortic valve leaflets when placing sutures in the anterior portion of the mitral valve annulus. A partial ring limits this concern. Some surgeons have now abandoned the use of a partial ring because in some cases, patients have experienced dilation of the fibrous anterior tissue. As a result, many other surgeons now employ a complete ring.

Complete rings can be constructed at the operating table by the surgeon or purchased as a preconstructed product under the name Medtronic/Duran Annuloplasty Ring. Still, in many cases anterior ring reinforcement is not required, and therefore partial rings are used in some patients. Partial rings can be constructed at the operating table and are also commercially available under the name Baxter/Cosgrove Annuloplasty Ring.

In some cases, the decision to use a partial or complete ring is a matter of surgeon preference. In other cases, the condition of the patient's natural valve annulus is taken into account by the surgeon upon exposure of the valve during the operative procedure. The situation results in the need for both partial and complete rings to be available to the surgeons within any given hospital. This results in added expense for the hospital, both in terms of inventory investment and storage space required to make both types of rings available. Further, the surgeon must make the choice between a partial or complete ring before the first anchoring stitches are placed into the ring.

There are several other known annuloplasty ring devices. U.S. Pat. No. 3,656,185 discloses a cardiac valvular prosthesis, e.g., for the mitral valve, consisting solely of an annular or part-annular member adapted to fit against the base of the cusps of a human heart valve and suture means for securing the member in place. The prosthesis cooperates with the natural valve cusps of the patient to form the valve. This device is a semi-rigid ring with a shape that matches the correct anatomical shape of the native valve, allowing remodeling of the valve.

U.S. Pat. No. 4,042,979 discloses an adjustable valvuloplasty ring that comprises a C-shaped frame that is sized and shaped to extend about the circumference of the left atrioventricular orifice along the base of the anterior cusp of the mitral valve; an expandable sleeve connected to the frame that together therewith forms a closed annulus, the sleeve being adapted to extend about the remainder of the circumference of the orifice; and a drawstring running through the sleeve by which the sleeve may be contracted to constrict and remodel the orifice and secured in place to maintain such constriction. This ring is entirely flexible.

U.S. Pat. No. 4,290,151 discloses an adjustable annular prosthesis for use in the surgical correction of atrioventricular orifice defects. This ring allows adjustment of the two sides of the ring independently, rather than just allowing the reduction of the ring.

U.S. Pat. No. 4,489,446 discloses a heart valve prosthesis incorporating a dynamic stiffener element. The prosthesis is adapted for securing to the annulus of an atrioventricular valve and has the characteristic of allowing normal movement of the annulus during the cardiac cycle while providing mechanical support to the valve annulus so as to maintain the valve leaflets in proper physiological alignment. The stiffener element has a plurality of reciprocating members allowing it to be modifiable in shape so as to be capable of assuming the optimum shape for a particular heart valve. This ring is an adjustable semi-rigid ring.

In U.S. Pat. No. 5,061,277, a support for a natural heart valve is disclosed. The support is generally ring shaped and has a size and shape to fit against the natural heart valve annulus. A posterior length of the support is flexible, and an anterior length of the support is semi-rigid. Accordingly, when the support is implanted, the support can shape the heart valve annulus and the first length of the support allows contraction of the heart valve annulus therealong.

U.S. Pat. No. 5,104,407 discloses an annuloplasty ring prosthesis which is formed from a selectively flexible body element having at least one defined length about its circumference which is substantially rigid. The remainder of the body element gradually increases in flexibility. The body element is a substantially annular shaped body element which is designed to be sutured to the annulus of a heart valve. The body element is formed from a non-corrosive, anti-magnetic material, and is wrapped in a material through which sutures can be drawn to suture the prosthesis to the heart valve annulus. This ring includes an out-of-plane portion on the anterior side.

U.S. Pat. No. 5,306,296 discloses adjustable and flexible atrioventricular annuloplasty rings containing circumferential radiopaque markers with mitral and tricuspid valve variations. A variant of the ring for use in the mitral region incorporates a curved framework in the anterior segment. The framework member is to maintain the intratrigonal and anterior leaflet distance during implantation. It is curved to prevent aortic outflow tract obstruction. Two or more pairs of drawstrings allow adjustment of four segments of the posterior portion of the mitral valve annulus. The variant of the ring for use in the tricuspid region incorporates a single drawstring to allow adjustment of the posterior left and right segment of the ring at implantation. The flexible contractile body of the ring common to both variants is of a biocompatible cloth. This ring includes a semi-rigid anterior region and a flexible posterior portion. The size of the ring is adjustable on both sides of the annulus.

U.S. Pat. No. 5,593,424 discloses implanting a series of devices which reduce the circumference of a diseased cardiac valve annulus or vascular structure to the desired size. Specifically, disclosed is a method and apparatus that maintains the normal shape of a vessel or induces the vessel to regain its normal shape. This facilitates localized reduction of the annulus without the use of a ring or a partial ring.

U.S. Pat. No. 5,716,397 discloses a fully flexible annuloplasty ring which is temporarily stiffened during implantation by inserting a withdrawable stiffening wire into a lumen of the ring. The annuloplasty ring has a lumen which is able to hold the stiffener prior to and during insertion. The stiffener includes a portion extending out of the lumen which can be pulled to withdraw the stiffener once the implant has been implanted. Thus, this ring has a removable rigid element allowing the ring to be rigid at the time of implantation to facilitate suture placement and remodeling of the annulus. Most wire stent valves use a single wire stent. Small diameter wires improve flexibility but are easily deformed. Plastic stents can lose their shape as a result of stent creep, and can also yield to an undesirable shape when exposed to extreme loads. Therefore, what is needed is a valve stent that retains flexibility, shape and durability and which can be used in various cardiac valvular prostheses.

SUMMARY

One embodiment, accordingly, provides a multi-filament stent which is sufficiently flexible to endure large deformations while retaining shape and durability. To this end, a stent includes a stent member formed by a plurality of adjacent filaments. The filaments are bound together.

A principal advantage of this embodiment is that multiple filaments are used to provide sufficient resistance to bending from either operation handling or in-service stress. The use of a multi-filament stent allows the stent to endure large deformations without experiencing a plastic change in the relaxed or at rest shape.

BRIEF DESCRIPTION OF THE DRAWING FIGURES

DETAILED DESCRIPTION

Figure 1:
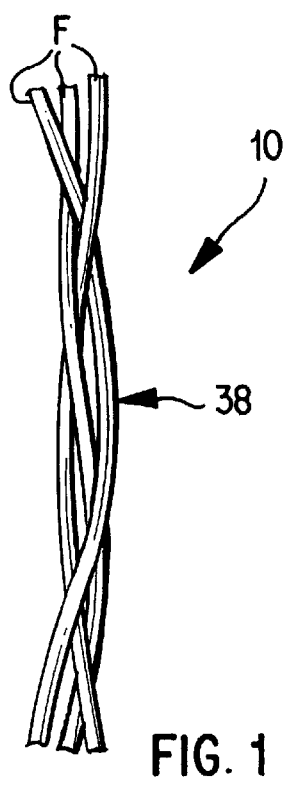
FIG. 1 is a view illustrating an embodiment of a braided multi-filament strand.
Figure 3:
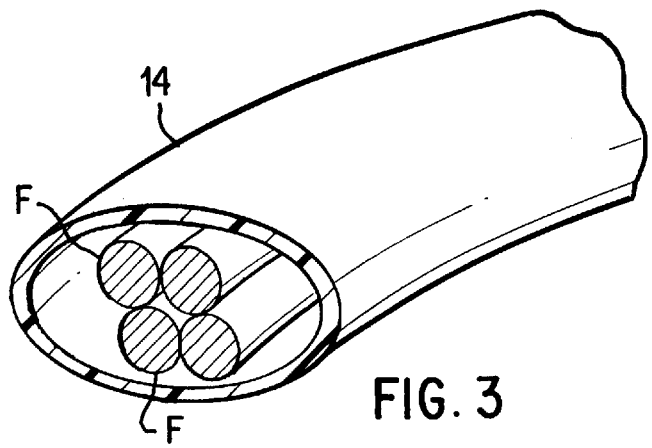
FIG. 3 is a view illustrating an embodiment of a multi-filament strand retained in a tubular member.
Figure 2:
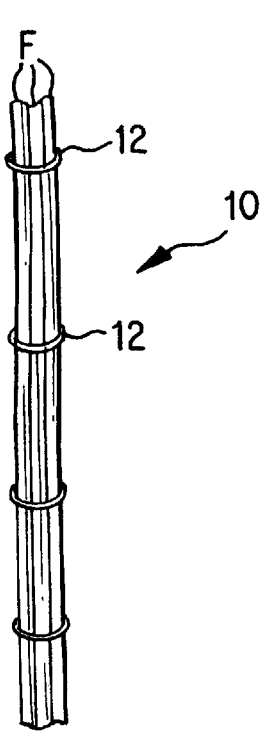
FIG. 2 is a view illustrating an embodiment of a multi-filament strand bound together by sutures.
Figure 4:
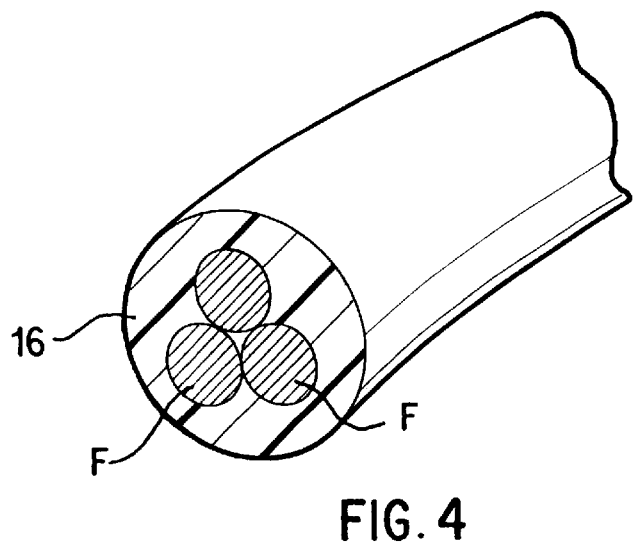
FIG. 4 is a view illustrating an embodiment of a multi-filament strand encapsulated in a synthetic material.
Figure 5:
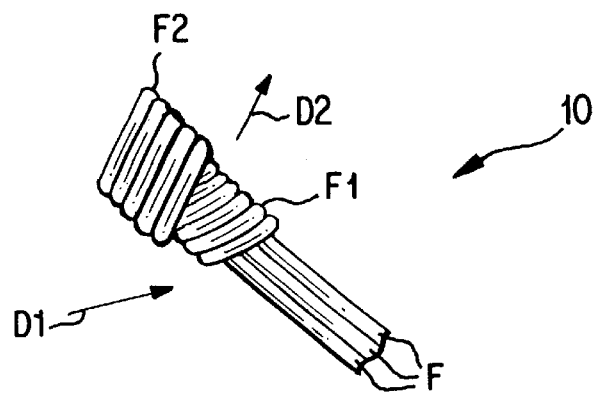
FIG. 5 is a view illustrating an embodiment of a multi-filament strand bound together by opposite windings.

A stent comprises a cable-shaped stent member 10, FIG. 1, formed by a plurality of adjacent filaments F. The filaments F are bound together by various means. For example, the filaments F may be bound together by braiding FIG. 1, by a plurality of sutures 12, FIG. 2, by a tubular sleeve member 14, FIG. 3, or by being encapsulated in a synthetic material 16, FIG. 4. The filaments F of stent member 10 may also be bound together by including at least one elongated filament F, FIG. 5, having a first filament F1 spirally wrapped around the elongated filament F and biased in a first direction D1, and a second filament F2 spirally wrapped around the first filament F1 and biased in a second direction D2 different from the first direction D1. The spirally wrapped stent member 10 may then be encapsulated in a polymer adhesive to retain the required form.

Figure 6:
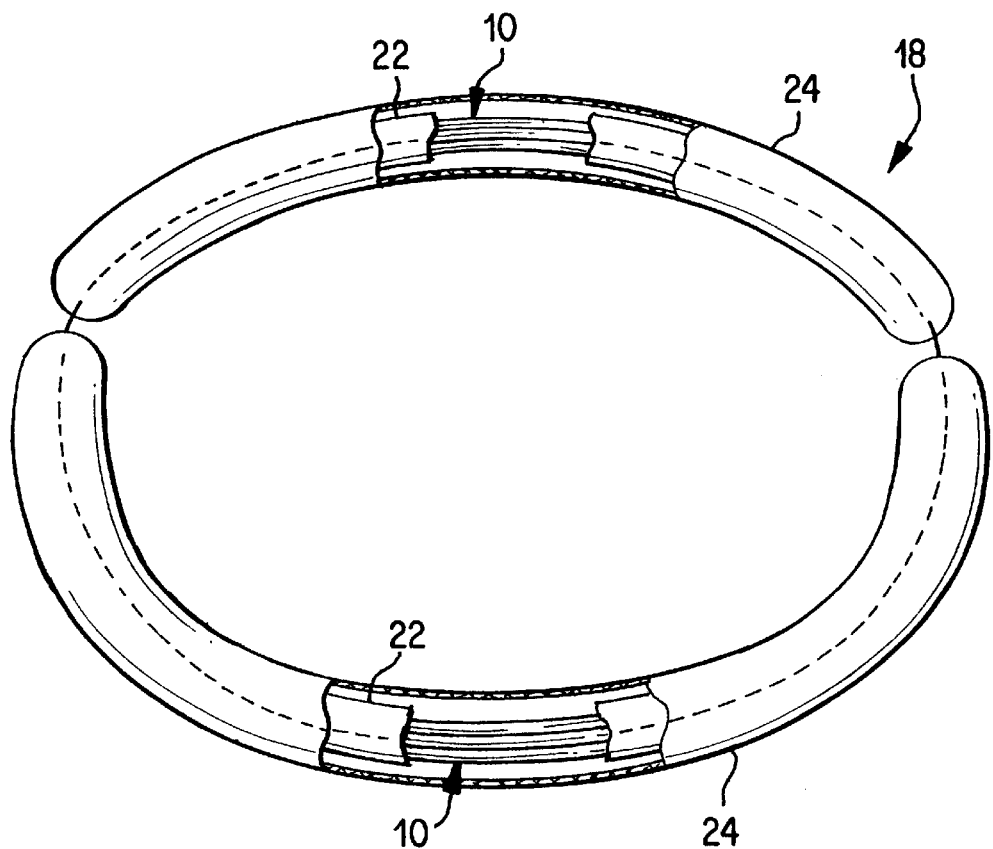
FIG. 6 is a view illustrating an embodiment of an annuloplasty ring including a multi-filament stent member.
Figure 7:
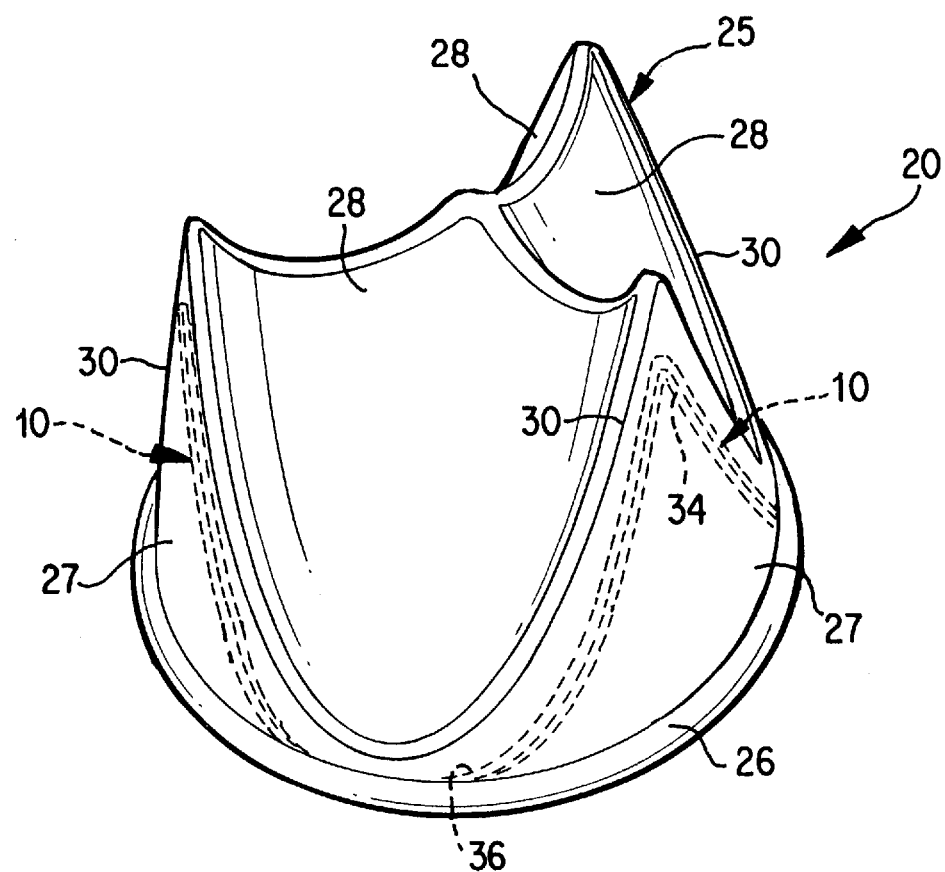
FIG. 7 is a view illustrating an embodiment of a flexible heart valve including a multi-filament stent member.

The stent member 10 may be formed in any of the above-mentioned manners for use in a cardiac valvular prosthetic member such as an annuloplasty ring 18, FIG. 6, or in a flexible heart valve 20, FIG. 7.

The annuloplasty ring 18, FIG. 6, generally has a shape which corresponds to the normal anatomical shape of a mitral or tricuspid valve annulus, and may be a segmented ring, for example. The general structure of such rings 18, includes an inner tubular member 22, an outer polyester member 24, and a shape maintaining, flexible stiffener or stent member 10, formed by one of the embodiments described herein, within the tubular member 22.

The flexible heart valve 20, FIG. 7, is usually formed as a one-piece molded biocompatible polymer body 25 having a base 26, a plurality of flexible leaflets 28, a plurality of shaped posts 30 having a thickness greater than the thickness of the leaflets 28, and a multi-filament flexible stent member 10 formed by one of the embodiments described herein, for providing flexible reinforcement to the valve body 25. The stent member 10 may be molded into the valve body 25 or may be secured to an outer surface 27 of the body 25 such as by sutures 12, or the like, not shown in FIG. 7. Stents 10 for flexible heart valves 20 include a plurality of post members 34 interconnected by a stent portion 36.

Figure 8:
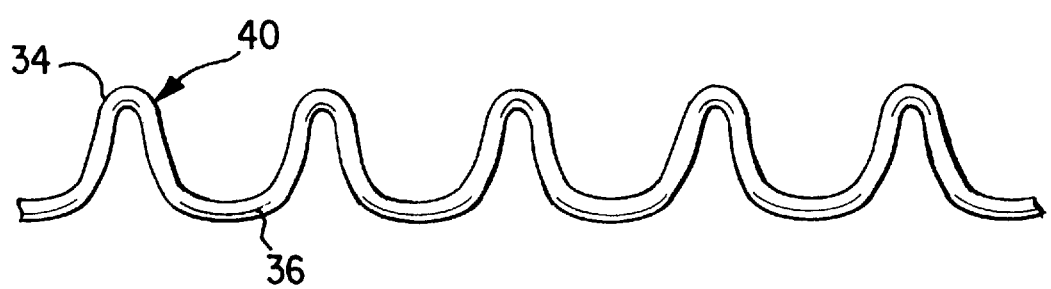
FIG. 8 is a view illustrating an embodiment of a single wire form which may be coiled to form a multi-filament stent.
Figure 9:
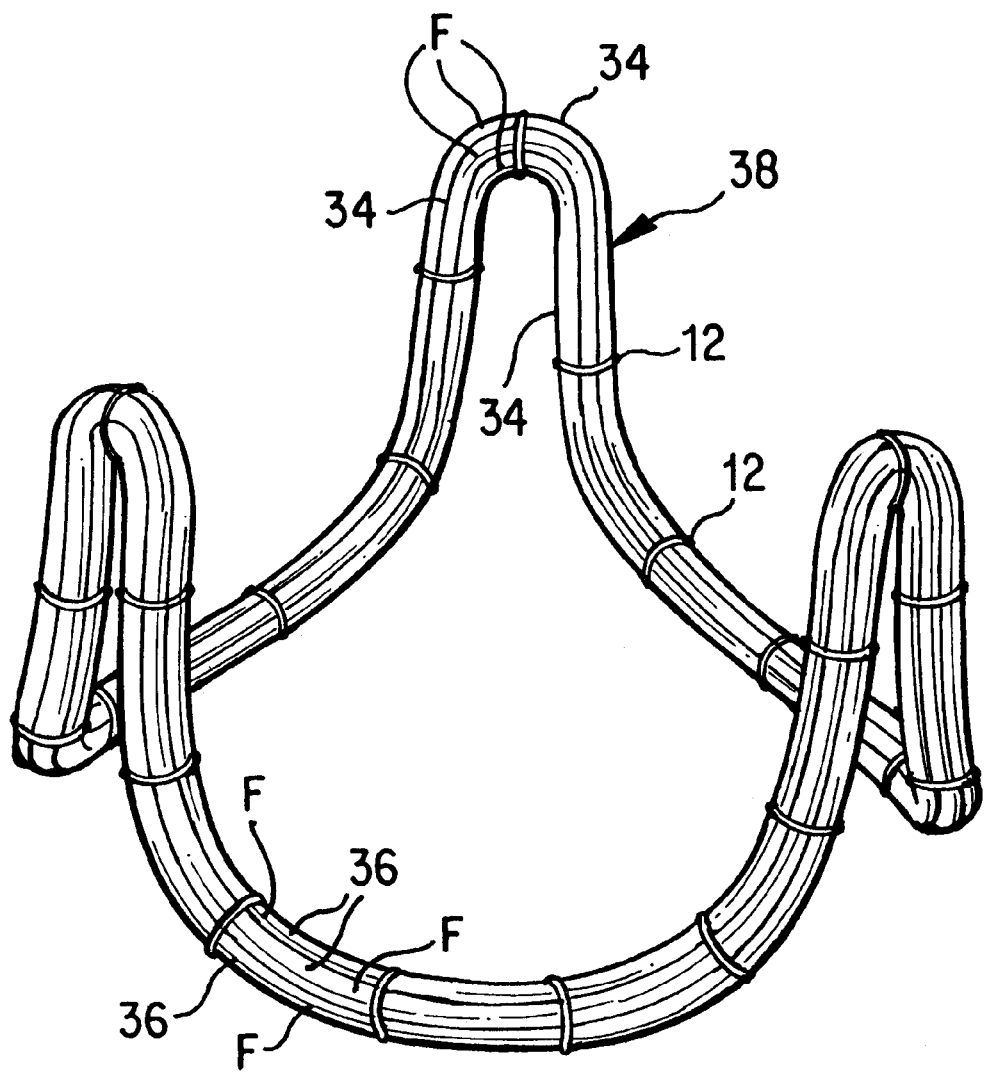
FIG. 9 is a view illustrating an embodiment of a multi-filament stent formed from the single filament wire form.

The previously mentioned manners in which the multiple filaments F may be bound together may include the braiding together of a plurality of filaments F, FIG. 1, into a filament strand 38. A single filament wire form 40, FIG. 8, including a plurality of post members 34 and stent portions 36 may be coiled, FIG. 9, into a multi-filament strand 38 so that a post member 34 of one filament F is aligned side-by-side with a post member 34 of each adjacent filament F, and a stent portion 36 of the one filament F is also aligned, side-by-side with the stent portion 36 of each adjacent filament F. Any of the previously mentioned multiple filament stents may be bound together by sutures 12 spaced apart at suitable intervals. The polymer 16 may be used to encapsulate the multiple filaments F, FIG. 4. The multiple filaments F may be inserted into the tubular member 14 for retaining the multiple filaments F together. The braided multiple filaments F, FIG. 1 are in a bound together form, but may additionally be inserted into the tubular member 14, FIG. 3 or may be encapsulated in the polymer 16, FIG. 4, or other biocompatible synthetic material if desired.

The filaments may be formed of a composite graphite/polymer providing a stent member that will have better fatigue strength than metal or polymer stents currently used, and will not have any machining stress or crack propagating characteristics that could lead to a failure. Regardless of the stent design, the stent member is preferably formed of continuous filaments of either impregnated or non-impregnated graphite composite, a carbon-polymer, a carbon-carbon, a polymer-polymer, or a ceramic filament.

As a result, one embodiment provides a stent including a stent member formed by a plurality of adjacent filaments. The filaments are bound together.

Another embodiment provides a prosthetic cardiac valvular member formed of a flexible material. A stent member is connected to the valvular member. The stent member is formed from a plurality of adjacent filaments which are bound together.

A further embodiment provides a method of forming a stent from a plurality of adjacent filaments. The adjacent filaments are bound together.

As it can be seen, the principal advantages of these embodiments are that multiple small diameter filaments are used rather than a single wire. Each individual filament can bend further without exceeding the elastic limit of the material because the distance from the outer element of the small filament to the neutral axis is smaller than with a single wire that is large enough in diameter to handle the applied load. Multiple filaments are used to provide sufficient resistance to bending from either operator handling or in-service stress. The use of a multi-filament stent will allow the stent to endure extremely large deformations without experiencing a plastic change in the relaxed shape. The stress seen by each filament will also be reduced so the resistance to fatigue failure from any given load will be improved. The filaments could be twisted or braided together. They could also be held together by a suture or cloth wrapped around the wires. Multiple filaments could also be held together in a mold for encapsulation by a polymer material that could hold the filaments together after molding.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A stent comprising:
   a stent member;
   the stent member being formed by a plurality of adjacent filaments; and
   a plurality of sutures binding the plurality of filaments together.

2. A cardiac valve prosthetic member comprising:
   a cardiac valvular member formed of flexible material;
   a stent member connected to the cardiac valvular member;
   the stent member being formed by a plurality of adjacent filaments; and
   the filaments being bound together and formed of a composite graphite-polymer material.

3. The valve as defined in claim 2 wherein the stent member is molded into the valve member.

4. The valve as defined in claim 2 wherein the stent member is secured to a surface of the valve member.

5. The valve as defined in claim 2 wherein the filaments are bound together by braiding.

6. The valve as defined in claim 2 wherein the filaments are bound together by a plurality of sutures.

7. The valve as defined in claim 2 wherein the filaments are bound together by a sleeve member.

8. The valve as defined in claim 2 wherein the filaments are bound together by being encapsulated in a synthetic material.

9. The valve as defined in claim 2 wherein the adjacent filaments include at least one elongated filament, a first filament spirally wrapped around the elongated filament in a first direction, and a second filament spirally wrapped around the first filament in a second direction opposite the first direction.

10. The valve as defined in claim 2 flirter comprising a plurality of flexible post members formed in the stent member.

11. The valve as define in claim 10 further comprising a stent portion interconnecting each adjacent post member.

12. The valve as defined in claim 2 wherein the cardiac valvular member is a flexible heart valve.

13. The stent as defined in claim 1 wherein the stent member is used in an annuloplasty ring.

* * * * *